United States Patent [19]
Sue

[11] Patent Number: 6,053,168
[45] Date of Patent: Apr. 25, 2000

[54] LIP SEAL ORAL DEVICE

[76] Inventor: Steven K. Sue, P.O. Box 10515, Honolulu, Hi. 96816

[21] Appl. No.: 09/399,110

[22] Filed: Sep. 20, 1999

Related U.S. Application Data

[63] Continuation-in-part of application No. 08/932,045, Sep. 17, 1997.
[51] Int. Cl.$^7$ ....................................................... A61C 5/14
[52] U.S. Cl. ........................................... 128/859; 128/860
[58] Field of Search .................................... 128/846, 848, 128/859–862; 602/902

[56] References Cited

U.S. PATENT DOCUMENTS

| | | |
|---|---|---|
| 2,483,157 | 9/1949 | Singer . |
| 3,871,370 | 3/1975 | McDonald ............................. 128/136 |
| 4,169,473 | 10/1979 | Samelson . |
| 4,672,959 | 6/1987 | May et al. . |
| 4,718,662 | 1/1988 | North . |
| 4,997,182 | 3/1991 | Kussick . |
| 5,584,687 | 12/1996 | Sullivan et al. . |
| 5,592,951 | 1/1997 | Castagnaro et al. . |

*Primary Examiner*—Michael A. Brown
*Attorney, Agent, or Firm*—Terrance L. Siemens

[57] ABSTRACT

An oral device for holding the tongue pressed against the roof of the mouth, thereby promoting suction closing the lips and encouraging breathing through the nose. The device has upper and lower U-shaped channels for engaging the upper and lower teeth of the user. The channels each include a vertical wall and indentations configured to receive the teeth in close cooperation. The lower tooth engaging member includes a vertical wall located inside the teeth which completes front and rear surrounding of the teeth, to hold the device in proper position. A planar platform projects horizontally and rearwardly from the U-shaped channels. This platform is located at the level of the bottom surfaces of the upper teeth, and supports the tongue. The platform has a relief configured to enable the tongue to pass comfortably over the rear surface of the platform when coming to rest thereon.

5 Claims, 2 Drawing Sheets

LIP SEAL ORAL DEVICE

REFERENCE TO RELATED APPLICATION

This application is a Continuation-In-Part of Ser. No. 08/932,045, filed Sep. 17, 1997.

BACKGROUND OF THE INVENTION

1. Field of the Invention

The present invention relates to physiological devices worn within the mouth for supporting the tongue and lips in appropriate positions for promoting effective and efficient physiological functions, such as breathing, particularly for the purpose of eliminating snoring. The device cooperates with the upper and lower teeth and provides a platform supporting the tongue. Usage of this device will encourage breathing through the nose, so that vibration of tissues within the mouth or breathing passages will not occur.

2. Description of the Prior Art

The tongue, lips, and other parts of the mouth exert significant influences on breathing and ancillary functions of the body. Efficiency of breathing and air flow within the mouth and other breathing passages maximizes physiological functions, such as athletic activities, and night time breathing. In particular, unimpeded air flow during sleep is characteristic of those who do not snore when sleeping. Tissues of structure associated with the mouth and breathing passages can deform over time due to age or due to various congenital or induced conditions of infirmity. These tissues may become displaced responsive to these conditions, and may come to interfere with breathing.

Prophylactic devices for reversing adverse effects of displaced tissue have been proposed in the prior art. In particular, benefit of supporting the tongue within the mouth has long been recognized as leading to improvement of various debilitating conditions. Devices which are worn in the mouth and affect position of the tongue have been proposed as leading to eliminating snoring, improving breathing, and other benefits.

U.S. Pat. No. 4,169,473, issued to Charles F. Samelson on Oct. 2, 1979, describes a device which cooperates with upper and lower teeth for support, and which has a tubular member open at one end for receiving and supporting the tongue. This device constrains the tongue to occupy a central position between the teeth, rather than supporting the tongue above the level at which upper teeth meet lower teeth, as occurs in the present invention.

A device for directing the tongue is shown in U.S. Pat. No. 4,997,182, issued to Leon Kussick on Mar. 5, 1991. This device lacks the horizontal tongue supporting member of the present invention.

U.S. Pat. No. 5,584,687, issued to Maureen P. Sullivan et al. on Dec. 17, 1996, illustrates a device intended to overcome clenching of the teeth. The subject device has right and left pads which absorb force from the teeth. These pads are connected by an arched member extending from right to left and projecting upwardly against the roof of the mouth. By contrast, the present invention has a single, U-shaped member corresponding to the pads. A horizontal member projects inwardly from the U-shaped member. The present invention thus supports the tongue at a level roughly even with and parallel to the upper teeth. By contrast, the arched member of Sullivan et al. is located above the tongue and avoids contact therewith, rather than influencing position of the tongue as occurs in the present invention.

An oral device seen in U.S. Pat. No. 5,592,951, issued to Vincent Castagnaro et al. on Jan. 14, 1997, provides U-shaped channels for engaging both upper and lower teeth, and an arched member projecting inside of and spanning these channels. By contrast, the member projecting inside the tooth engaging channel of the present invention is flat and horizontal. Also, the tooth engaging member of the present invention engages only the upper teeth, whereas the device of Castagnaro et al. engages both upper and lower teeth.

Oral devices are also shown in U.S. Pat. Nos. 2,483,157, issued to John L. Singer on Sep. 27, 1949, 4,672,959, issued to Robert H. May et al. on Jun. 16, 1987, and 4,718,662, issued to Richard B. North on Jan. 12, 1988. These devices lack the tooth engaging structure combined with the tongue supporting platform as these components are configured in the present invention.

None of the above inventions and patents, taken either singly or in combination, is seen to describe the instant invention as claimed.

SUMMARY OF THE INVENTION

The present invention provides a device for supporting the tongue in a suitable position for maintaining sealing of the lips and mouth during ordinary breathing. A significant benefit accruing from the invention includes causing the user to breath through the nose. Snoring is eliminated or minimized.

The novel oral device seals the mouth when the mouth is closed thereover. The device holds the tongue in a position establishing an effective seal under these conditions. Structure of the device includes upper and lower U-shaped channels each of which receives, respectively, the upper and lower teeth of a person in close cooperation. The device is substantially immobilized when entrapped between the upper and lower teeth when the mouth is closed.

A platform projects horizontally from the interior surfaces of the U-shaped channel at a level corresponding to that even with the bottom surfaces of the teeth. This platform supports the tongue, and extends rearwardly to a projection line spanning the user's bicuspid teeth. The tongue rests on the platform, and is held in a position against the roof of the mouth, thereby establishing an effective seal preventing or severely limiting passage of air into the breathing passages through the mouth, by mild suction between the tongue and the roof of the mouth. The user is obliged to breath through the nose.

The device is formed from a form holding yet flexible material which assures that it will fit closely to the mouth. A slot formed in the platform opens to the rear, to relieve undue intrusion into the soft tongue. This feature as well as flexibility contribute to comfort. If the device is fabricated sufficiently strongly, it may be employed as a guard in athletic activities.

Accordingly, it is a principal object of the invention to provide a mouthpiece for holding the tongue against the roof of the mouth.

It is another object of the invention to promote breathing through the nose.

It is a further object of the invention to eliminate or reduce snoring in persons breathing through the mouth.

It is an object of the invention to provide improved elements and arrangements thereof in an apparatus for the purposes described which is inexpensive, dependable and fully effective in accomplishing its intended purposes.

These and other objects of the present invention will become readily apparent upon further review of the following specification and drawings.

BRIEF DESCRIPTION OF THE DRAWINGS

Various other objects, features, and attendant advantages of the present invention will become more fully appreciated as the same becomes better understood when considered in conjunction with the accompanying drawings, in which like reference characters designate the same or similar parts throughout the several views, and wherein.

DETAILED DESCRIPTION OF THE PREFERRED EMBODIMENTS

Figure 1:
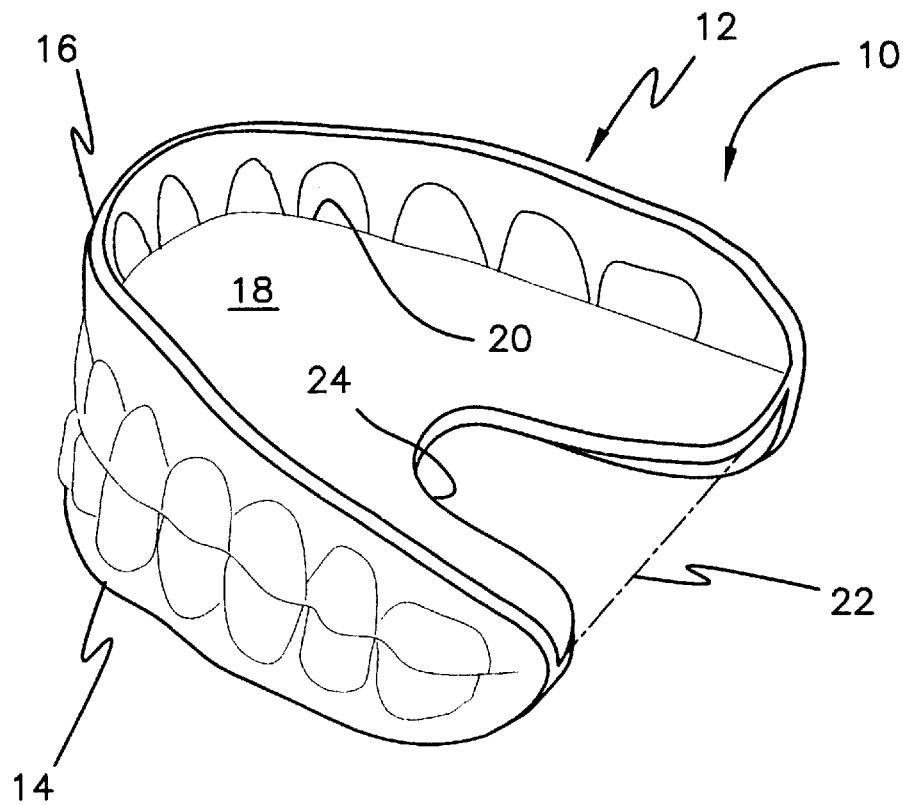
FIG. 1 is a diagrammatic, side perspective view of a first embodiment of the invention.
Figure 2:
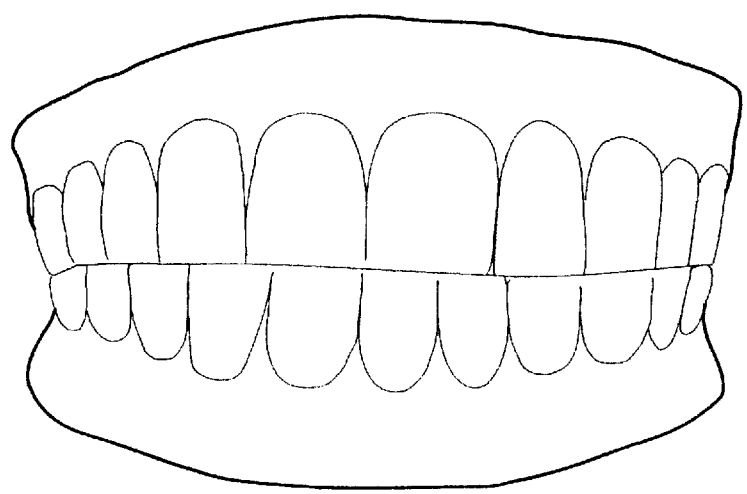
FIG. 2 is a front elevational view of the embodiment of FIG. 1.
Figure 3:
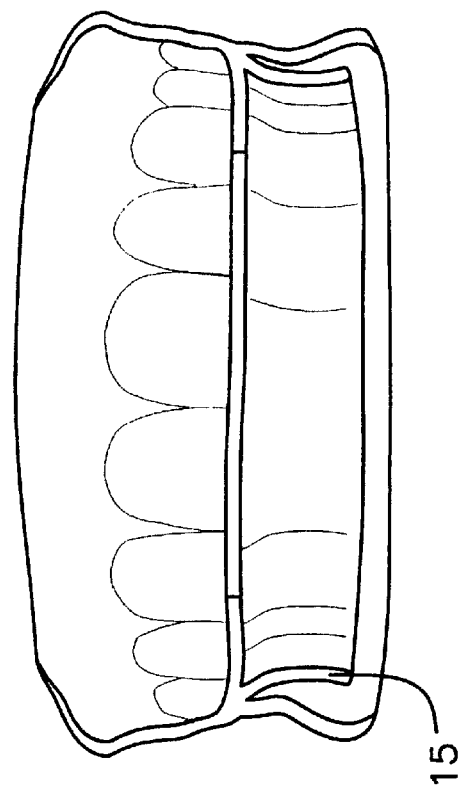
FIG. 3 is a rear elevational view of the embodiment of FIG. 1.
Figure 4:
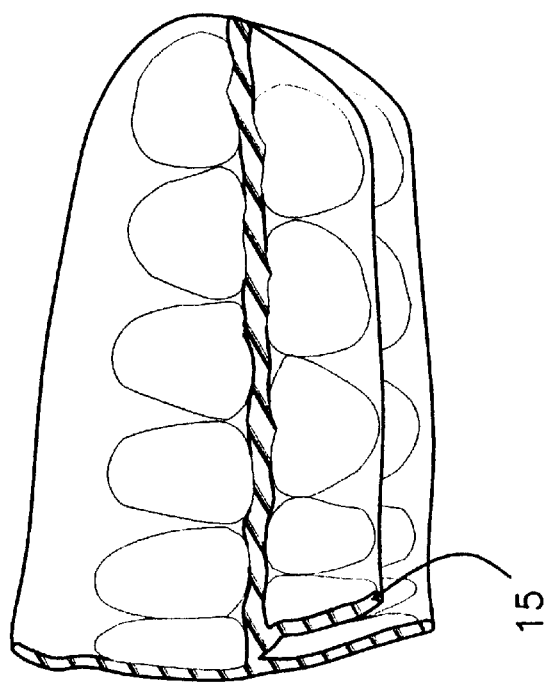
FIG. 4 is a side elevational view of FIG. 1, taken in cross section to show the right side of the invention.

FIGS. 1–4 of the drawings show the novel oral device 10 for placing and maintaining a user's tongue (not shown) in a desired position in contact with both the hard and soft palate of the user (neither shown). Device 10 comprises a single U-shaped upper tooth engagement member 12 dimensioned and configured to cooperate closely with and partially surround the outside surfaces of the user's upper teeth such that the tongue is maintained in the desired position wherein the tongue is in contact with both the hard and soft palate of the mouth, when the mouth is closed over device 10. The outside surfaces of the upper teeth include the front surfaces of the front teeth, the right side surfaces of the right teeth, and the left side surfaces of the left teeth.

A corresponding single U-shaped lower tooth engagement member 14 is dimensioned and configured to cooperate closely with the user's lower teeth (not shown). Lower tooth engagement member 14 is joined to and depends from upper tooth engagement member 12, and is aligned with upper tooth engagement member 12 such that the user can close his mouth when oral device 10 is worn in the mouth. The user's upper teeth will be received in close cooperation within upper and lower tooth engagement members 12, 14. Lower tooth engagement member 14 preferably includes a supplementary tooth engaging member 15 located, dimensioned, and configured to cooperate closely with the inside surfaces of the user's lower teeth. The inside surfaces are those at the rear of the front teeth, those at the left side of the right teeth, and those at the right side of the left teeth. It will be appreciated that whereas the user's tongue will serve as a stop preventing rearward movement of device 10, no corresponding situation acts on lower tooth engagement member 14. Therefore, supplementary tooth engaging member 15 (see FIGS. 3 and 4) completes lateral encirclement of the lower teeth to complement entrapment of the upper teeth.

Upper tooth engagement member 12 includes an unbroken, generally vertical peripheral wall 16 extending around an outer portion of said upper tooth engagement member and enclosing the outer portion of the user's teeth and gums.

A substantially planar tongue lift platform 18 extends rearwardly into the user's mouth. For purposes of this discussion, the front of device 10 is that side visible from an observer facing the user's face. The rear is that side relatively closer to the rear of the user's head. Tongue lift platform 18 is attached around an inner portion 20 of upper tooth engaging member 12. This assures that tongue lift platform 18 is located at a level immediately above lower tooth engaging member 14. Tongue lift platform 18 extends rearwardly at least to a line 22 extending between the user's bicuspid teeth (not shown), thus holding the tongue in the desired position in contact with both the hard and soft palate of the mouth, and preventing the user from breathing through the mouth.

A relief groove 24 is provided to prevent an uncomfortable situation wherein the tongue would otherwise be forced to make an abrupt bend to project above and forwardly of tongue platform 18. Groove 24 relieves a straight line that would be assumed by the rearmost vertical surface of platform 24 if groove 24 were not present. The purpose of groove 24 is to allow a portion of the tongue to depend from the tip of the tongue without having to conform to the straight line which would otherwise exist. Groove 24 is concave and opens rearwardly. It is preferred that the minimum distance that platform extends back into the mouth is equal to the length of a line drawn from the user's bicuspid teeth, the fourth tooth counting back from the incisors.

Preferably, concave indentations are formed in both upper and lower tooth engaging members 14, 16. Indentations correspond to configuration of individual teeth. This configuration assures close cooperation between device 10 and the teeth, thereby enhancing adherence of device 10 to the mouth by engaging the teeth. Indentations are readily molded by those skilled in the dental arts, and the process of creating indentations closely conforming to the teeth of a particular person need not be set forth in detail herein.

The depiction of FIG. 1 also reveals a nominally flat upper surface and nominally flat lower surface of platform 24. The upper and lower surfaces are nominally flat in that a perfect planar surface is not required. It is merely desired that the tongue and other tissues of the mouth pass relatively unobstructed over these surfaces.

Comfort is still further enhanced by forming device 10 from a flexible, partially rigid synthetic material. The material is sufficiently flexible to bend under manual pressure, but partially rigid in that it will hold its configuration absent manual or equivalent pressure acting to deform its configuration as shown in the drawings. Suitable materials may be selected from silicones and synthetic resins, including those conventionally employed to form castings and impressions for dental and other purposes.

The present invention is susceptible to variations and modifications which may be introduced without departing from the inventive concept. Illustratively, it would be possible to truncate the full U-shaped configuration of the channel by engaging fewer than all of the upper teeth. However, the savings in material and complexity is insignificant, and further entails loss of engaging contact with the teeth such that successful engagement could be threatened. In addition, the front portion of the U shape provides a wall interfering with excessive forward projection of the tongue. The tongue position is limited by the lingual or rear side of the upper front teeth, and therefore will contribute to successful use in some individuals who might otherwise defeat successful use by forward projection of the tongue. It is preferred, therefore, to configure the channel as fully U-shaped and configured to partially surround all teeth of one jaw.

It is to be understood that the present invention is not limited to the embodiments described above, but encompasses any and all embodiments within the scope of the following claims.

I claim:

1. An oral device for placing and maintaining a user's tongue in a desired position in contact with both the hard and soft palate of the user, comprising:

a single U-shaped upper tooth engagement member dimensioned and configured to cooperate closely with the outside surfaces of the user's upper teeth such that the tongue is maintained in the desired position wherein the tongue is in contact with both the hard and soft palate of the mouth when the mouth is closed over said oral device;

a single U-shaped lower tooth engagement member dimensioned and configured to cooperate closely with the outside surfaces of the user's lower teeth, wherein said lower tooth engagement member is joined to said upper tooth engagement member and aligned with said upper tooth engagement member such that the user can close his mouth when said oral device is worn in the mouth, and the user's upper teeth will be received in close cooperation within said U-shaped upper tooth engagement member and the user's lower teeth will be received in close cooperation with said U-shaped lower tooth engagement member proximate the user's upper teeth; and a substantially planar tongue lift platform extending horizontally and rearwardly into the user's mouth, said tongue lift platform being attached around an inner portion of said single U-shaped upper tooth engaging member, wherein said tongue lift platform is located at a level immediately above said U-shaped lower tooth engaging member, thus holding the tongue in the desired position wherein the tongue is in contact with both the hard and soft palate of the mouth, and preventing the user from breathing through the mouth.

2. The oral device according to claim 1, wherein said tongue lift platform extends rearwardly at least to a line extending between the user's bicuspid teeth.

3. The oral device according to claim 1, wherein said lower tooth engagement member includes a supplementary tooth engaging member located, dimensioned, and configured to cooperate closely with the inside surfaces of the user's lower teeth.

4. The oral device according to claim 1, wherein said tongue lift platform includes a concave relief groove which opens rearwardly.

5. The oral device according to claim 1, wherein said oral device is formed from a partially rigid synthetic material.

* * * * *